(12) United States Patent
Levy et al.

(10) Patent No.: US 11,938,343 B2
(45) Date of Patent: Mar. 26, 2024

(54) CAVITATION-ENHANCED TARGETED DRUG DELIVERY AND DOSING

(71) Applicant: INSIGHTEC, LTD., Tirat Carmel (IL)

(72) Inventors: Yoav Levy, Hinanit (IL); Kobi Vortman, Haifa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 913 days.

(21) Appl. No.: 16/622,005

(22) PCT Filed: Jun. 29, 2018

(86) PCT No.: PCT/IB2018/000811
§ 371 (c)(1),
(2) Date: Dec. 12, 2019

(87) PCT Pub. No.: WO2019/002940
PCT Pub. Date: Jan. 3, 2019

(65) Prior Publication Data
US 2021/0146157 A1    May 20, 2021

Related U.S. Application Data

(63) Continuation-in-part of application No. 15/637,163, filed on Jun. 29, 2017, now Pat. No. 11,123,575.
(Continued)

(51) Int. Cl.
*A61N 7/02* (2006.01)
*A61B 5/00* (2006.01)
(Continued)

(52) U.S. Cl.
CPC ............ *A61N 5/1049* (2013.01); *A61B 5/489* (2013.01); *A61B 34/10* (2016.02);
(Continued)

(58) Field of Classification Search
CPC ................. A61M 37/0092; A61N 7/02; A61N 2007/0039; A61N 2007/0052;
(Continued)

(56) References Cited

U.S. PATENT DOCUMENTS

| 2004/0122323 A1 | 6/2004 | Vortman et al. |
| 2007/0016039 A1 | 1/2007 | Vortman et al. |

(Continued)

FOREIGN PATENT DOCUMENTS

| CN | 105682739 A | 6/2016 |
| EP | 2343103 A1 | 7/2011 |

(Continued)

OTHER PUBLICATIONS

Jolesz FA. MRI-guided focused ultrasound surgery. Annu Rev Med. 2009;60:417-30. doi: 10.1146/annurev.med.60.041707.170303. PMID: 19630579; PMCID: PMC4005559 (Year: 2009).*

(Continued)

*Primary Examiner* — Bill Thomson
*Assistant Examiner* — Aminah Asghar
(74) *Attorney, Agent, or Firm* — Morgan, Lewis & Bockius LLP

(57) ABSTRACT

Various approaches for disrupting target tissue for treatment include identifying a target volume of the target tissue; causing disruption of the target tissue in a region corresponding to the target volume so as to increase tissue permeability therein; computationally generating a tissue permeability map of the target volume; and based on the tissue permeability map, computationally evaluating the disruption of the target tissue within the target volume.

18 Claims, 8 Drawing Sheets

Related U.S. Application Data

(60) Provisional application No. 62/526,548, filed on Jun. 29, 2017, provisional application No. 62/526,545, filed on Jun. 29, 2017, provisional application No. 62/526,550, filed on Jun. 29, 2017, provisional application No. 62/597,073, filed on Dec. 11, 2017, provisional application No. 62/597,076, filed on Dec. 11, 2017.

(51) Int. Cl.

| | |
|---|---|
| *A61B 34/10* | (2016.01) |
| *A61M 37/00* | (2006.01) |
| *A61N 5/10* | (2006.01) |
| *A61N 7/00* | (2006.01) |
| *A61B 6/00* | (2006.01) |
| *A61B 6/03* | (2006.01) |
| *A61B 6/12* | (2006.01) |

(52) U.S. Cl.
CPC ......... *A61M 37/0092* (2013.01); *A61N 5/103* (2013.01); *A61N 5/1039* (2013.01); *A61N 5/1048* (2013.01); *A61N 5/1064* (2013.01); *A61N 7/02* (2013.01); *A61B 5/4836* (2013.01); *A61B 6/03* (2013.01); *A61B 6/12* (2013.01); *A61B 6/504* (2013.01); *A61N 2005/1052* (2013.01); *A61N 2005/1055* (2013.01); *A61N 2005/1058* (2013.01); *A61N 2005/1061* (2013.01); *A61N 2005/1087* (2013.01); *A61N 2005/1092* (2013.01); *A61N 2005/1098* (2013.01); *A61N 2007/0004* (2013.01); *A61N 2007/0039* (2013.01); *A61N 2007/0052* (2013.01); *A61N 2007/0082* (2013.01); *A61N 2007/027* (2013.01)

(58) Field of Classification Search
CPC .... A61N 5/1049; A61N 5/103; A61N 5/1039; A61N 5/1048; A61N 5/1064; A61N 2005/1055; A61N 2005/1098; A61N 2007/0004

See application file for complete search history.

(56) References Cited

U.S. PATENT DOCUMENTS

| | | | |
|---|---|---|---|
| 2008/0221382 A1* | 9/2008 | Karshafian | A61N 7/00 600/2 |
| 2010/0143241 A1* | 6/2010 | Johnson | A61K 49/223 424/9.4 |
| 2012/0116221 A1 | 5/2012 | Sehgal et al. | |
| 2013/0046229 A1* | 2/2013 | Konofagou | A61B 8/0808 604/22 |
| 2013/0331685 A1* | 12/2013 | Liu | A61N 7/02 601/2 |
| 2013/0331738 A1 | 12/2013 | Borelli | |
| 2014/0343421 A1 | 11/2014 | Kim et al. | |
| 2014/0378737 A1 | 12/2014 | Carpenter et al. | |
| 2015/0196638 A1 | 7/2015 | Czarnota et al. | |
| 2017/0043149 A1* | 2/2017 | Liu | A61M 37/0092 |
| 2019/0350486 A1* | 11/2019 | Walczak | A61B 5/055 |
| 2020/0323515 A1 | 10/2020 | Levy | |
| 2021/0187331 A1 | 6/2021 | Zadicario et al. | |

FOREIGN PATENT DOCUMENTS

| | | |
|---|---|---|
| EP | 2676702 A1 | 12/2013 |
| WO | WO2010118307 A1 | 10/2010 |
| WO | WO2013034709 A1 | 3/2013 |
| WO | WO2014/053950 A1 | 4/2014 |
| WO | WO2014118632 A1 | 8/2014 |

OTHER PUBLICATIONS

Park et al., Evaluation of permeability, doxorubicin delivery, and drug retention in a rat brain tumor model after ultrasound-induced blood-tumor barrier disruption, Journal of Controlled Release, vol. 250, Mar. 28, 2017, pp. 77-85 (Year: 2017).*

Chai et al., Magnetic-resonance imaging for kinetic analysis of permeability changes during focused ultrasound-induced blood-brain barrier opening and brain drug delivery, Journal of Controlled Release, vol. 192, Oct. 28, 2014, pp. 1-9 (Year: 2014).*

International Search Report and Written Opinion of the International Searching Authority dated Nov. 28, 2018 for International Application No. PCT/IB18/000811 (17 pages).

Vlachos, F. et al., "Permeabiity Assessment of the Focused Ultrasound-Induced Blood-Brain Barrier Opening Using Dyanamic Contrast-Enhanced MRI", Phys. Med. Biol. 55 (2010) 5451-5466, 16 pages.

International Search Report and Written Opinion of the International Searching Authority dated Nov. 19, 2018 for International Application No. PCT/IB18/000841 (11 pages).

International Search Report and Written Opinion of the International Searching Authority dated Nov. 12, 2018 for International Application No. PCT/IB18/000834 (12 pages).

Extended European Search Report, EP18180302.4, dated Nov. 21, 2018, 5 pgs.

Decision to Grant, EP18180302, dated Jan. 30, 2020, 2 pgs.

Decision to Grant, EP18768933, dated Jul. 1, 2021, 3 pgs.

Insightec, Ltd., Allowance Notification for Invention, CN201880043567. 3, dated Jan. 30, 2022, 2 pgs.

Vortman, Office Action, U.S. Appl. No. 15/637,163, dated May 13, 2019, 15 pgs.

Vortman, Office Action, U.S. Appl. No. 15/637,163, dated Dec. 6, 2019, 12 pgs.

Vortman, Office Action, U.S. Appl. No. 15/637,163, dated May 21, 2020, 14 pgs.

Vortman, Final Office Action, U.S. Appl. No. 15/637,163, dated Sep. 18, 2020, 15 pgs.

Vortman, Notice of Allowance, U.S. Appl. No. 15/637,163, dated May 28, 2021, 11 pgs.

Insightec, Ltd., International Search Report and Written Opinion of the International Searching Authority dated Nov. 23, 2020 for International Application No. PCT/IB2020/000677, 17 pgs.

Insightec, Ltd., Communication Pursuant to Article 94(3), EP18768933. 6, dated Sep. 20, 2021, 4 pgs.

First Office Action, CN201880056389, dated Feb. 1, 2021, 19 pgs.

Second Office Action, CN201880056389, dated Aug. 30, 2021, 19 pgs.

First Office Action, CN201880043399.8, dated Feb. 2, 2021, 7 pgs.

Notification to Grant Patent Right for Invention, CN201880043399-8, dated Aug. 30, 2021, 3 pgs.

De Picciotto, Notice of Allowance, U.S. Appl. No. 16/622,004, dated May 5, 2022, 9 pgs.

* cited by examiner

CAVITATION-ENHANCED TARGETED DRUG DELIVERY AND DOSING

CROSS-REFERENCE TO RELATED APPLICATION

This application is a U.S. National Phase Application of PCT/M2018/000811, filed Jun. 29, 2018, which claims priority to, and the benefit of, U.S. patent application Nos. 62/526,548 (filed on Jun. 29, 2017), 62/526,545 (filed on Jun. 29, 2017), 62/526,550 (filed on Jun. 29, 2017), 15/637,163 (filed on Jun. 29, 2017), 62/597,073 (filed on Dec. 11, 2017), and 62/597,076 (filed on Dec. 11, 2017). The entire disclosures of these priority documents are hereby incorporated by reference.

FIELD OF THE INVENTION

The invention relates generally to targeted drug delivery and, more particularly, to systems and methods for enhancing the targeted drug delivery using an ultrasound procedure.

BACKGROUND

Drug-delivery systems are frequently developed with the objectives of lowering the overall administered therapeutic dose of a pharmaceutical, increasing its residence time, prolonging its release over time, and enhancing the targeting of diseased tissues. The toxic effects of drugs can be reduced by increasing the concentration or dose in the target region while limiting the concentration or dose in non-target regions. Accordingly, targeted drug-delivery systems direct relatively high levels of drug to a focal site, thereby minimizing drug uptake by non-target organs or tissues and lowering the costs of therapy.

One conventional approach to enhancing targeted drug delivery involves the use of ultrasound. For example, exposing target tissue to ultrasound may increase its permeability, allowing a higher proportion of a drug dose to exert a therapeutic effect on the target region. In another approach, drugs are encapsulated in "nanobubbles" that are injected to the target region; application of ultrasound may cause a local increase in temperature and bubble cavitation, thereby triggering release of the encapsulated drug. Similarly, ultrasound energy may be applied to chemically activate drugs administered into the target region. While these conventional approaches may improve targeted drug delivery, numerous challenges remain.

For example, to ensure that application of ultrasound results in increased permeability in the target tissue only (and has no clinically significant effects on the permeability of non-target tissue), ultrasound beams are required to be precisely focused onto the target location. However, because of the body's heterogeneous anatomy (with, e.g., skin, skull or ribs located between the ultrasound transducer array and the target region), it is difficult to focus ultrasound beams precisely onto the target region as planned, for example, in an earlier preparatory stage. In addition, because the size of the target region is generally larger than that of the ultrasound focal zone, multiple sonications are necessary to generate a plurality of focal zones that collectively cover the target region. However, because the human body is flexible and moves even when a patient is positioned to keep still (due to respiration, for example, or small involuntary movements), the focal region created by multiple sonications over time—even when delivered within seconds of each other—may deviate from the target region. Deviation of the focal region from the target region may undesirably increase permeability in the non-target region with adverse therapeutic consequences.

Accordingly, there is a need for improved targeted drug-delivery approaches that accommodate a patient's anatomy and movement during delivery, release and/or activation of drugs for treatment.

SUMMARY

The present invention provides systems and methods for increasing tissue permeability in a target region using an ultrasound procedure; tissue regions with altered permeability are accurately tracked via use of a permeability map. In various embodiments, the permeability map is generated using an MRI contrast agent selected based on the molecular size of the therapeutic agent to be administered for treatment. For example, the target tissue may normally be permeable to molecules having a size less than 400 Daltons, but the therapeutic agent may have a size of 1,000 Daltons and therefore is blocked from entering the target region. Upon application of ultrasound, tissue in the target region may be disrupted, and consequently, the permeability thereof may be increased. The permeability level and/or the size of the tissue region in which the permeability has been increased may depend on the intensity and/or duration of the ultrasound application. Accordingly, by adjusting ultrasound parameters, the tissue permeability of the target region can be increased to a desired degree to allow the therapeutic agent to penetrate and/or diffuse therein. An MRI contrast agent having substantially the same molecular weight (or other size metric) as the therapeutic agent (i.e., 1,000 Daltons in this example) may then be injected into the target region in order to generate the tissue permeability map. The size of the MRI contrast agent ensures that it can penetrate the sonicated target tissue, resulting in a contrast change visible in MRI images. Accordingly, by monitoring the contrast change in the MRI images, a map of the permeability of the tissue at the target and/or non-target region can be generated.

In one embodiment, microbubbles are optionally generated (e.g., acoustically) at and/or injected into the target region in accordance with conventional practice. Application of ultrasound pulses to the microbubbles may result in an array of behaviors known as acoustic cavitation, which can assist in tissue disruption and thereby increase tissue permeability at the target region. Accordingly, in one embodiment, the tissue permeability map is generated based at least in part on a localized acoustic response (e.g., an instantaneous acoustic response level, a cumulative acoustic response dose, and/or a spectral distribution of the acoustic response) from the microbubbles at the target and/or non-target regions during the ultrasound procedure.

Additionally or alternatively, the permeability map may be created using a computational simulation. For example, the simulation may create the permeability map based on a tissue model of the material characteristics (e.g., heat sensitivity and/or thermal energy tolerance) of the target and/or non-target tissue, the characteristics (e.g., the administration profile, size distribution, concentration, etc.) of the microbubbles, and/or the ultrasound parameters (e.g., the amplitude, frequency, duration of the sonication pulses, etc.). These characteristics may be determined empirically, by reference to the literature, etc.

In various embodiments, the tissue region with increased permeability in the permeability map is compared against (e.g., registered to an image of) the target region defined prior to the ultrasound procedure to verify that the tissue permeability in the defined target region has increased to allow penetration of the therapeutic agent therein. In addition, tissue permeability in the non-target region preferably remains substantially unchanged (e.g., any permeability change is clinically insignificant in the sense that any resulting drug penetration does not have a clinically adverse effect) and thereby blocks the entry path of the therapeutic agent so as to ensure precise delivery, release and/or activation of the therapeutic agent at the desired target region only. In some embodiments, if the tissue region having an increased permeability (as revealed by the map) is smaller than the defined target region, additional sonication may be performed to increase the volume of increased tissue permeability so that it encompasses target region. If, however, the mapped region is larger than the defined target region, the patient may rest for one or two days until the tissue at the target region has regenerated and lost the induced permeability (and so can be disrupted again from the baseline level). Once the mapped region is verified to substantially (e.g., ±5% or ±10% by volume) match the defined target region, the therapeutic agent may be administered to the target region for treatment.

Alternatively, if the therapeutic agent has already been administered based on a permeability map, it may not be necessary to obtain and verify a new map for a subsequent administration. For example, the therapeutic agent may be administered into the target region based on the tissue permeability map created after the first series of ultrasound sonications; subsequent ultrasound sonications may be applied to the target region that has the therapeutic agent therein. Because the therapeutic agent may itself exhibit responsiveness to sonication and/or enhance disruption rate of the target tissue, this approach may advantageously increase the uptake rate (including, for example, the penetration rate, release rate and/or activation rate) of the therapeutic agent in the target region.

Accordingly, the present invention provides approaches for creating a tissue permeability map of the target region and, if desired, of non-target regions. Based thereon, a therapeutic agent may be administered with enhanced targeting. In addition, because ultrasound can penetrate deep into the body and generate a focused beam at a desired region in a controlled manner, increasing the tissue permeability using ultrasound allows the therapeutic agent to be precisely delivered to and/or activated within the target region.

Accordingly, in one aspect, the invention pertains to a system for disrupting target tissue for treatment and evaluating disruption of the target tissue. In various embodiments, the system includes an imaging device for acquiring a digital representation of one or more portions of a target volume of the target tissue; an ultrasound transducer for generating and delivering one or more sonications of shaped energy beams to the target volume for causing disruption of the target tissue in a region corresponding to the target volume so as to increase tissue permeability therein; and a controller, responsive to the imaging device, configured to generate a tissue permeability map indicating regions of increased tissue permeability and estimates of the tissue permeability due to the disruption and to computationally evaluate, based on the tissue permeability map, the disruption of the target tissue within the target volume. In one implementation, the controller is further configured to generate the tissue permeability map based at least in part on MRI contrast imaging, planning or simulation of the sonication(s), and/or an acoustic response of the target volume during the disruption.

In some embodiments, the controller is further configured to computationally determine, based on the tissue permeability map, whether tissue within the target volume can admit a therapeutic agent. For example, the controller may be configured to computationally determine whether tissue within the target volume can admit the therapeutic agent based on a molecular size thereof and the estimated tissue permeability. In addition, the controller may be further configured to computationally verify, based on the tissue permeability map, that tissue outside the target volume cannot admit the therapeutic agent to a clinically significant degree. In one embodiment, the controller is further configured to compare a target volume in the tissue permeability map to the target volume acquired using the imaging device. In some embodiments, the system further includes an administration device for administering the therapeutic agent only when tissue within the target volume can admit the therapeutic agent and the target volume substantially matches the target volume acquired using the imaging device.

Additionally or alternatively, the system may include an administration device for administering the therapeutic agent into the target volume based on the tissue permeability map. The controller may be further configured to cause the ultrasound transducer to generate and deliver the second sonication(s) of shaped energy beams to the target volume after administering the therapeutic agent. In various embodiments, the tissue permeability map includes multiple permeability levels, each permeability level associated with a tissue region in the target volume and indicating a maximal size of molecules capable of entering the associated tissue region. The administration device may then be configured to administer the therapeutic agent based on the permeability levels. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U.

In some embodiments, the imaging device is further configured to acquire an image of the target volume during delivery of the sonication(s) and the controller is further configured to adjust a parameter associated with a subsequent sonication based on the image. In addition, the controller may be further configured to cause the ultrasound transducer to generate multiple sonications each delivering shaped acoustic energy to one focal zone in the target volume, the focal zones collectively being coextensive with the target volume. The sonication(s) may cause generation and cavitation of microbubbles in the target volume. Additionally or alternatively, the system may further include an administration device for administering a microbubble seed to the target volume; the sonication(s) and the microbubble seed cause generation of the microbubbles. Further, the system may further include an administration device for administering microbubbles to the target volume; the sonication(s) may then cause cavitation of the microbubbles.

In another aspect, the invention relates to a method of disrupting target tissue for treatment and evaluating disruption of the target tissue. In various embodiments, the method includes the steps of (a) identifying a target volume of the target tissue; (b) causing disruption of the target tissue in a region corresponding to the target volume so as to increase tissue permeability therein; (c) computationally generating a tissue permeability map indicating regions of increased tissue permeability and estimates of the tissue permeability due to the disruption; and (d) based at least in part on the tissue permeability map and the identified target volume, computationally evaluating the disruption of the target tissue within the target volume. In one implementation, the tissue permeability map is generated based at least in part on MRI contrast imaging, planning or simulation of the sonication, and/or an acoustic response of the target volume during step (b).

In some embodiments, the method further includes computationally determining, based on the tissue permeability map, whether tissue within the target volume can admit a therapeutic agent. For example, whether tissue within the target volume can admit the therapeutic agent may be computationally determined based on a molecular size thereof and the estimated tissue permeability. In addition, the method may include computationally verifying, based on the tissue permeability map, that tissue outside the target volume cannot admit the therapeutic agent to a clinically significant degree. In one embodiment, step (d) includes comparing a target volume in the tissue permeability map to the target volume identified in step (a) and determining a match therebetween. The therapeutic agent is administered only when tissue within the target volume can admit the therapeutic agent and the target volume substantially matches the target volume identified in step (a).

Additionally or alternatively, the method may include administering the therapeutic agent into the target volume based on the tissue permeability map. The method may further include generating and delivering the second sonication(s) of shaped acoustic energy beams to the target volume after administering the therapeutic agent. In various embodiments, the tissue permeability map includes multiple permeability levels, each permeability level associated with a tissue region in the target volume and indicating a maximal size of molecules capable of entering the associated tissue region. The therapeutic agent may then be administered based on the permeability levels. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U.

In some embodiments, the method further includes generating and delivering one or more sonications of shaped energy beams to the target volume for causing the tissue permeability to increase. When multiple sonications are generated, each delivers shaped acoustic energy to one focal zone in the target volume, and the focal zones collectively are coextensive with the target volume. In addition, the method may include imaging the target volume during delivery of the first one of the sonications and, based thereon, adjusting a parameter associated with a subsequent one of the sonications. In one embodiment, the method includes causing cavitation of microbubbles in the target volume to increase the tissue permeability therein. The microbubbles may be injected into the target volume and/or generated by shaped acoustic energy beams. In one implementation, the microbubbles are generated by a microbubble seed injected to the target volume and shaped acoustic energy beams.

As used herein, the term "substantially" means ±10% by a tissue volume, and in some embodiments, ±5% by a tissue volume. "Clinically significant" means having an undesired (and sometimes the lack of a desired) effect on tissue that is considered significant by clinicians, e.g., triggering the onset of damage thereto. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
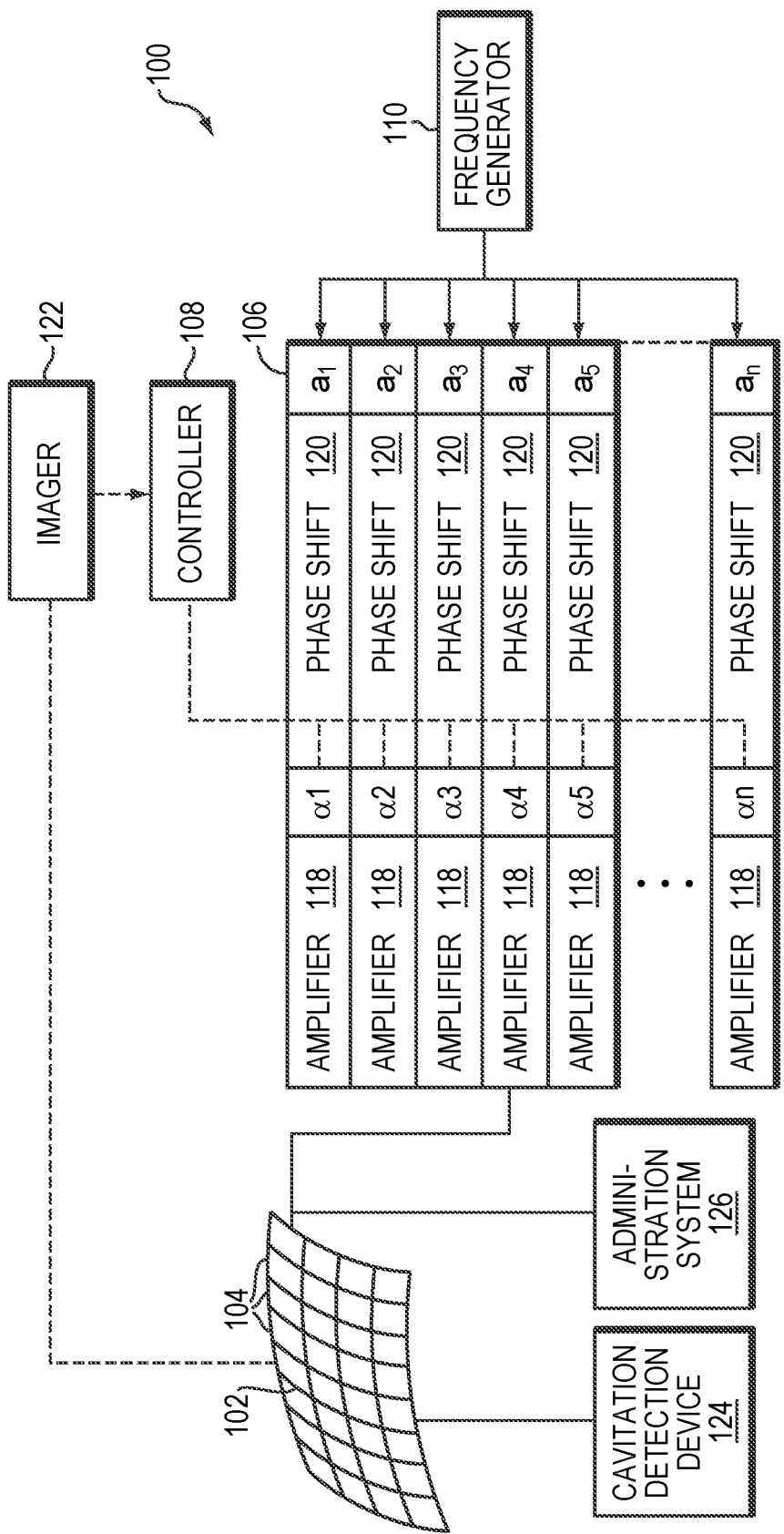
FIG. 1A schematically depicts an exemplary ultrasound system in accordance with various embodiments of the current invention.

FIG. 1A illustrates an exemplary ultrasound system 100 for generating and delivering a focused acoustic energy beam to a target region for disrupting the tissue and thereby causing the tissue permeability to increase therein. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50 Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radiofrequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radiofrequency generator 110 and the beamformer 106 are configured to drive the individual transducer elements 104 of the transducer array 102 at the same frequency, but at different phases and/or different amplitudes.

The amplification or attenuation factors a1-an and the phase shifts α1-αn imposed by the beamformer 106 serve to transmit and focus ultrasonic energy onto the target region, and account for wave distortions induced in the tissue located between the transducer elements 104 and the target region. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns at the target region. In certain embodiments, the computation is based on detailed information about the characteristics (e.g., structure, thickness, density, etc.) of the tissue located between the transducer element 104 and their effects on propagation of acoustic energy. Such information may be obtained from an imager 122. The imager 122 may be, for example, a magnetic resonance imaging (MRI) device, a computer tomography (CT) device, a positron emission tomography (PET) device, a single-photon emission computed tomography (SPECT) device, or an ultrasonography device. Image acquisition may be three-dimensional (3D) or, alternatively, the imager 122 may provide a set of two-dimensional (2D) images suitable for reconstructing a three-dimensional image of the target region and/or its surrounding region. In addition, the ultrasound system 100 and/or imager 122 may be utilized to detect the presence, type, and/or location associated with microbubble cavitation as further described below. Additionally or alternatively, the system may include a cavitation detection device (such as a hydrophone or suitable alternative) 124 to detect information associated with microbubble cavitation and an administration system 126 for parenterally introducing a therapeutic agent and/or microbubbles into the patient's body as further described below. The imager 122, the cavitation detection device 124, and/or the administration system 126 may be operated using the same controller 108 that facilitates the transducer operation; alternatively, they may be separately controlled by one or more separate controllers intercommunicating with one another.

Figure 1B:
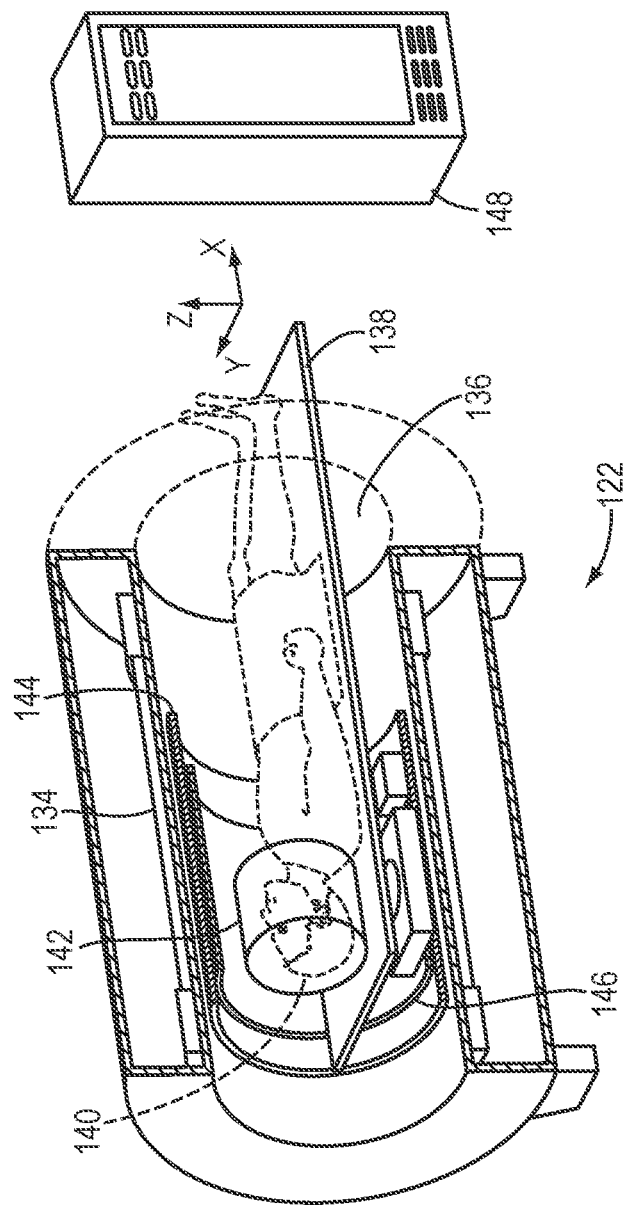
FIG. 1B schematically depicts an exemplary MRI system in accordance with various embodiments of the current invention.

FIG. 1B illustrates an exemplary imager—namely, an MRI apparatus 122. The apparatus 122 may include a cylindrical electromagnet 134, which generates the requisite static magnetic field within a bore 136 of the electromagnet 134. During medical procedures, a patient is placed inside the bore 136 on a movable support table 138. A region of interest 140 within the patient (e.g., the patient's head) may be positioned within an imaging region 142 wherein the electromagnet 134 generates a substantially homogeneous field. A set of cylindrical magnetic field gradient coils 144 may also be provided within the bore 136 and surrounding the patient. The gradient coils 144 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 146 surrounding the imaging region 142 emits RF pulses into the imaging region 142 to cause the patient's tissues to emit magnetic-resonance (MR) response signals. Raw MR response signals are sensed by the RF coil 146 and passed to an MR controller 148 that then computes an MR image, which may be displayed to the user. Alternatively, separate MR transmitter and receiver coils may be used. Images acquired using the MRI apparatus 122 may provide radiologists and physicians with a visual contrast between different tissues and detailed internal views of a patient's anatomy that cannot be visualized with conventional x-ray technology.

The MRI controller 148 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, the target region (e.g., a tumor) can be identified.

To perform targeted drug delivery, it is necessary to determine the location of the target region with high precision prior to drug administration. Accordingly, in various embodiments, the imager 122 is first activated to acquire images of the target region and/or non-target region (e.g., the healthy tissue surrounding the target region and/or the intervening tissue located between the transducer array 102 and the target region) and, based thereon, determine anatomical characteristics (e.g., a location, a size, a density, a structure and/or a shape) associated therewith. For example, a tissue volume may be represented as a 3D set of voxels (i.e., volumetric pixels) based on a 3D image or a series of 2D image slices and may include the target region and/or non-target region.

Figure 2:
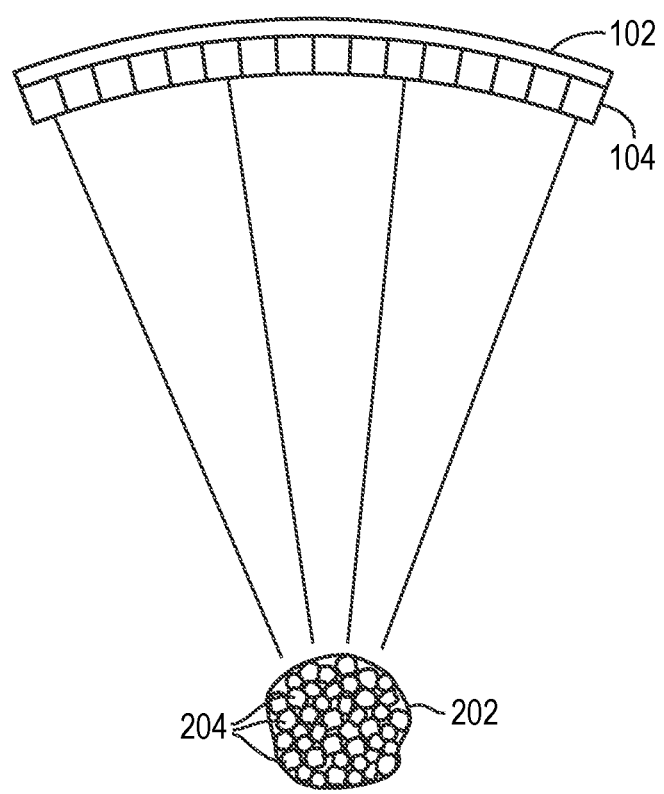
FIG. 2 depicts one or more focal zones of ultrasound waves/pulses generated in a target volume in accordance with various embodiments.

Referring to FIG. 2, in various embodiments, after the 3D voxel set corresponding to the target volume 202 is identified using the imager 122, the transducer array 102 is activated to generate a focal zone 204 in the target volume 202. Generally, the size of the target volume 202 is larger than that of the focal zone 204. Thus, the transducer array 102 may be sequentially activated to generate a plurality of focal zones 204 in the target volume 202 for disrupting the tissue therein, and thereby temporarily increasing permeability of the tissue. In addition, each focal zone 204 may be shaped (e.g., to a focal point or volume such as a sphere or a toroid) to conform to the local shape of the target region 202. Approaches to configuring the ultrasound transducer elements to generate a focal zone having a desired size and shape are provided, for example, in U.S. Pat. No. 7,611,462, the contents of which are incorporated herein by reference.

Generally, the degree of permeability and/or the size of the tissue region in which the permeability has been increased depend on the intensity and/or duration of the ultrasound application. Accordingly, by adjusting the ultrasound intensity and/or duration, the tissue permeability of the target region can be increased to a desired degree to allow the therapeutic agent to penetrate and/or diffuse therein. In some embodiments, the ultrasound procedure is monitored by the controller 108 based on image information from the imager 122 in real-time until the focal zones generated from the series of sonications collectively occupy the target volume 202, disrupt tissue within the target volume 202 and cause permeability of the tissue to be temporarily increased. In addition, the controller 108 may adjust an ultrasound parameter (e.g., frequency, power, application duration, etc.) of a subsequent series of sonications based on the image information acquired in the previous series of sonications.

Figure 3:
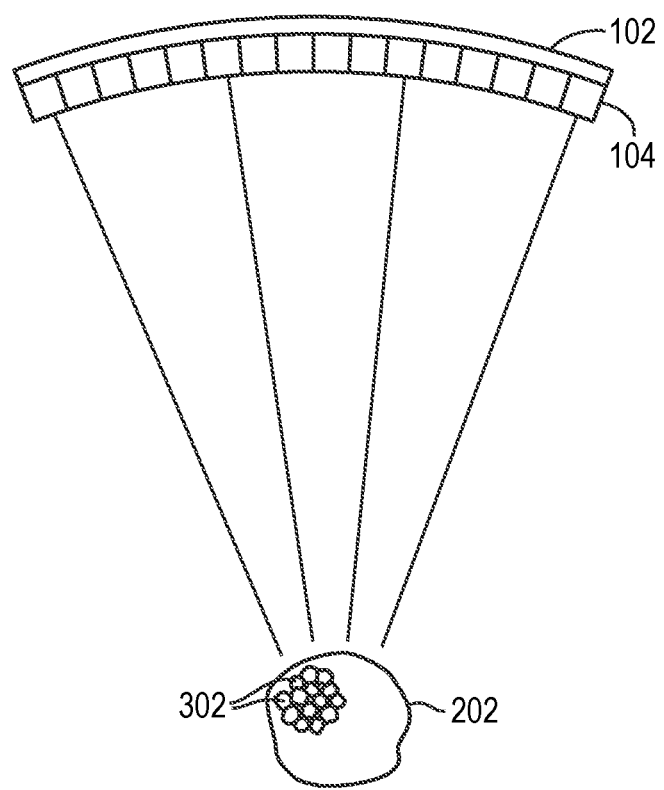
FIG. 3 depicts presence of microbubbles in a target tissue region in accordance with various embodiments.

Referring to FIG. 3, in various embodiments, the ultrasonic energy emitted by the transducer elements 104 may be above a threshold and thereby cause generation of a small cloud of gas bubbles (or "microbubbles") 302 in the liquid contained in the target region 202. The microbubbles 302 can be formed due to the negative pressure produced by the propagating ultrasonic waves or pulses, when the heated liquid ruptures and is filled with gas/vapor, or when a mild acoustic field is applied on tissue containing cavitation nuclei. At a relatively low acoustic power (e.g., 1-2 Watts above the microbubble-generation threshold), however, the generated microbubbles 302 tend to undergo oscillation with compression and rarefaction that are equal in magnitude and thus the microbubbles generally remain unruptured (i.e., a "stable cavitation"). At a higher acoustic power (e.g., more than 10 Watts above the microbubble-generation threshold), the generated microbubbles 302 undergo rarefaction that is greater than compression, which may cause inertial (or transient) cavitation of the microbubbles in which the microbubbles in the liquid rapidly collapse. The microbubble cavitation, in turn, may result in transient disruption of the tissue in the targeted region 202, and consequently increase tissue permeability in the target region. The degree of the permeability increase may depend on the microbubble concentration and/or the delivered acoustic power (or power density) and energy in the target region 202. Accordingly, a desired tissue permeability (i.e., to allow penetration/diffuse of the therapeutic agent) may be achieved by adjusting the microbubble characteristics (e.g., the concentration, administration profile, etc.) and/or ultrasound parameters (e.g., amplitude, frequency, application duration, etc.) as further described below.

In some embodiments, microbubbles are injected into the target region 202 to assist disruption of the tissue and thereby increase permeability thereof. The microbubbles may be introduced in the form of liquid droplets that subsequently vaporize, as gas-filled bubbles, or entrained with another suitable substance, such as a conventional ultrasound contrast agent. The injected microbubbles may themselves create or facilitate the creation of additional microbubbles. For example, the administration system 126 may introduce a seed microbubble into the target region 202, and the controller 108 may then cause the ultrasound waves/pulses to focus at a region proximate to the seed microbubble, thereby inducing generation of a microbubble cloud for disrupting the tissue at the target region 202. Therefore, the actual disrupting effect on the target tissue may result from a combination of the injected microbubbles and microbubbles additionally created in the tissue.

In some embodiments, the ultrasound-induced microbubble cavitation is utilized to transiently disrupt (or "open") a targeted blood-brain barrier (BBB) region. Opening the BBB has been found to reduce the amyloid plaque burden, thereby providing therapeutic value for Alzheimer's disease. In addition, disrupting the BBB region may allow the therapeutic agent present in the bloodstream to penetrate the "opened" BBB region and effectively deliver therapy to the targeted brain cells. Again, the degree and size of the BBB opening may be controlled by adjusting the microbubble characteristics and/or ultrasound parameters. For example, to effectively and efficiently cause generation and/or cavitation of the microbubbles in the target region 202, it may be desirable to maximize the amount of acoustic energy transmitted to the target region 202 while minimizing the exposure of healthy non-target tissue (e.g., tissue located between the transducer and target region) to ultrasound. Typically, the degree of ultrasound absorption in tissue is a function of frequency, given by:

$$I=I_0 e^{-2\alpha fz}$$

where $I_0$ is the ultrasound intensity at the point of entry into the tissue (measured in W/cm$^2$), I is the intensity after beam propagation through the tissue over a distance z (which is measured in cm), f is the frequency of the ultrasound (measured in MHz), and a is the absorption coefficient at that frequency (measured in cm$^{-1}$·MHz$^{-1}$). Higher values of the product of produce greater degrees of absorption in the target region but also larger fractions of ultrasound that are absorbed before reaching the target region. Therefore, at a certain depth, z, in tissue, the ultrasound frequency of the applied waves may reflect a trade-off between the absorption of the acoustic power in the path zone and the peak intensity at the focal zone. In some embodiments, an optimal ultrasound transmission frequency is determined based on the anatomical characteristics (e.g., type, size, location, property, structure, thickness, density, etc.) of the target and/or intervening tissue so as to achieve a peak intensity at the target region 202. Based thereon, the transducer elements can then be activated to cause generation and/or cavitation of the microbubbles. Approaches to determining an optimal frequency for the ultrasound application are provided, for example, in U.S. Patent Publication No. 2016/0008633, the contents of which are incorporated herein by reference.

In addition, if the microbubbles are pre-formed and introduced to the target volume 202 via the administration system 126, it may be desirable to select a size distribution thereof such that the microbubble resonance frequency differs from the ultrasound transmission frequency for avoiding damage of the non-target region. Generally, the smaller the radius of the microbubbles, the larger will be their resonance frequency. Accordingly, once the optimal ultrasound frequency is determined, the mean radius of microbubbles having a resonance frequency substantially equal to the ultrasound frequency may be determined. In one implementation, the size distribution of the pre-formed microbubbles is selected such that a significant fraction (e.g., more than 50%, 90%, 95%, or 99% or more) of the microbubbles have a radius below that corresponding to a resonance frequency equal to the applied ultrasound frequency. Preferably, the microbubble resonance frequency is substantially larger than the ultrasound frequency (e.g., by a factor of ten), but it can be substantially smaller than the ultrasound frequency, if desired. As a result, when the transducer elements 104 are activated with a low acoustic power, microbubbles at the non-target region are unresponsive to the relatively low acoustic field, whereas microbubbles at the target region (where the acoustic field is relatively high due to the focused beam) 202 may oscillate and/or collapse. Accordingly, this approach may disrupt tissue at the target volume 202 with high spatial accuracy and avoid undesired collateral damage to the healthy tissue surrounding the target. Approaches to determining and selecting a desired size distribution of microbubbles are provided, for example, in U.S. Patent Application entitled "Ultrasound Frequency and Microbubble Size Optimization in Microbubble-Enhanced Ultrasound Treatment" filed on even date herewith, the contents of which are incorporated herein by reference.

Figure 4A:
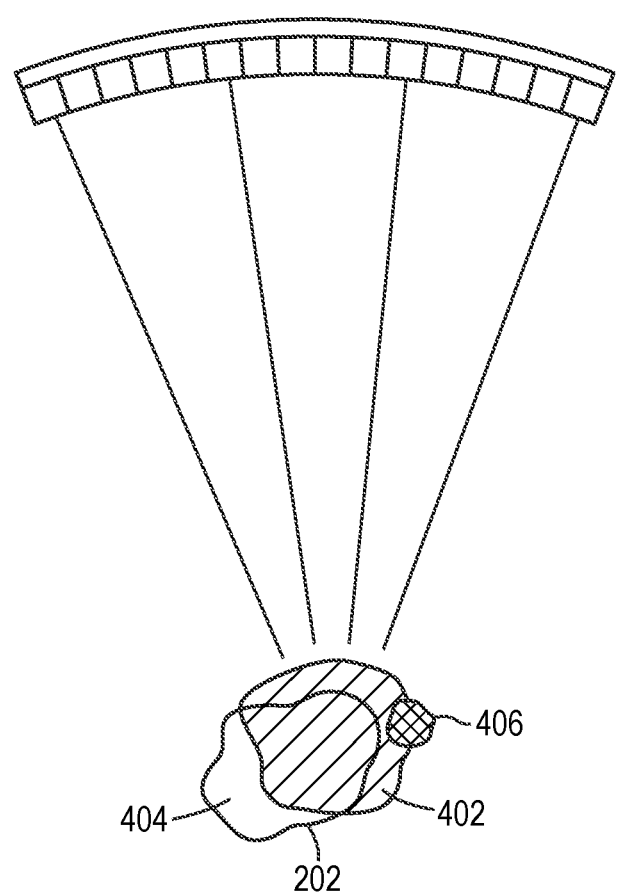
FIG. 4A depicts a comparison of a permeability map against a 3D voxel set of a target volume in accordance with various embodiments.
Figure 4B:
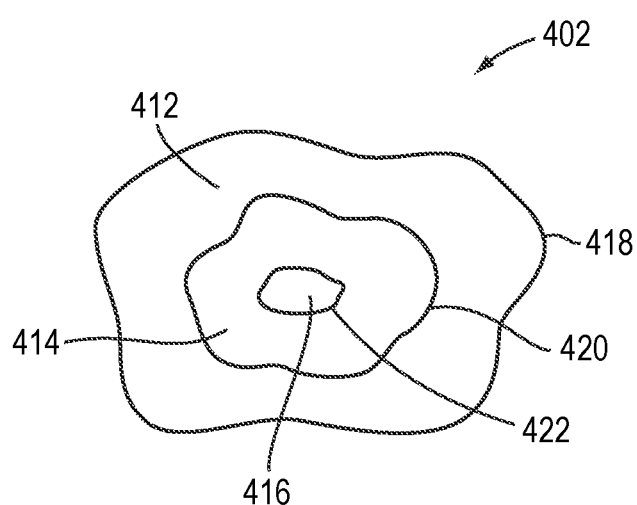
FIG. 4B depicts an exemplary permeability map in accordance with various embodiments.

Referring to FIG. 4A, in various embodiments, after the ultrasound procedure and prior to administration of the therapeutic drug, an image or a "map" 402 of the tissue permeability (or BBB opening) at the target region 202 and/or the surrounding healthy non-target tissue is created as described below. This map 402 is then compared against the 3D voxel set of the target volume 202 acquired (using the imager 122, for example) prior to the ultrasonic procedure in order to verify that the tissue permeability in the target region 202 has been increased sufficiently to allow the therapeutic drug to penetrate and/or diffuse therein, while the tissue permeability in the non-target region remains sufficiently unchanged to substantially block the therapeutic drug from entering (i.e., to prevent the drug from having a clinically significant effect in the non-target tissue). The permeability map 402 may include tissue permeability levels (e.g., permeability of molecules having various sizes) at the target and/or non-target region or, more specifically, openings of the BBB region and/or its surrounding region. For example, referring to FIG. 4B, MRI contrast agents having three molecular weights, $D_1$-$D_3$ ($D_1$<$D_2$<$D_3$) may be separately injected into the target region. The permeability map created thereby may indicate three regions 412-416: region 412 allows all MRI contrast agents having the three molecular weights to penetrate and diffuse therein, region 414 allows the MRI contrast agents having the molecular weights of $D_1$ and $D_2$ to penetrate and diffuse therein only; and region 216 allows only the MRI contrast agents having the molecular weight of $D_1$ to penetrate and diffuse therein. As a result, the permeability map 402 includes various levels 418-422 indicating the maximal sizes of molecules capable of entering each region of the tissue. This procedure may be performed with more or fewer than three contrast agents, of course.

If the mapped region 402 having a high tissue permeability substantially (e.g., within 1%, 5% or 10%) matches the 3D target volume 202 volumetrically (i.e., the regions 202, 402 are substantially coextensive spatially), the therapeutic drug may be administered. If the mapped region 402 having a high permeability is smaller than the defined target volume 202, additional sonication may be performed to increase tissue permeability at low-permeability portions 404 of the target region; the ultrasound-mediated permeability-increasing procedure may be continued until a substantial match between the mapped region having high-permeability and the defined target volume 202 is achieved. In some embodiments, when the high-permeability mapped region is larger than the defined 3D target volume 202 or when a sensitive organ 406 outside of the target volume 202 has high permeability, then depending on the toxicity of the therapeutic drug to be administered, the patient may be required to rest for one or two days until the disrupted tissue is regenerated (thereby reducing the tissue permeability to its normal state) and ready to be disrupted again.

The tissue permeability map 402 may be generated using an MRI contrast agent. For example, the MRI contrast agent may be selected based on the molecular size of the therapeutic agent as explained above. In various embodiments, the selected MRI contrast agent (preferably of substantially the same size as the therapeutic agent) is injected into the target region 202 using, for example, the administration system 126, to determine the tissue permeability therein. By monitoring the contrast change in the MRI images (due to penetration of the MRI contrast agent into the disrupted tissue), a map reflecting tissue permeability based on the size of the MRI contrast agent can be generated. In addition, by selecting and injecting into the target region 202 separately resolvable MRI contrast agents having different sizes, the map may indicate various levels of tissue permeability, each level indicating a specific maximal size of molecules capable of entering and diffusing in the tissue. In some embodiments, the 3D voxel set of the target volume 202 is acquired using an imaging system that is not MRI; as a result, image registration between two imaging systems may be necessary prior to the comparison. Approaches to registering images acquired using two or more imaging systems are provided, for example, in U.S. Pat. No. 9,934,570, the entire disclosure of which is hereby incorporated by reference.

Additionally or alternatively, the permeability map 402 may be established based at least in part on a localized acoustic response (e.g., an instantaneous acoustic response level, a cumulative acoustic response dose, and/or a spectral distribution of the acoustic response) from the microbubbles at the target region during the ultrasound procedure; the acoustic response may be detected using a cavitation detection device 124 (shown in FIG. 1) and/or the ultrasound transducer array 102. Generally, the volume of tissue whose permeability has been increased and/or the degree of the permeability increase correlates with the amount of microbubble cavitation in the target region 202. Thus, by detecting the acoustic response emanating from the microbubbles localized at the target region 202 and/or non-target region, the increase in tissue permeability and/or the size of the tissue having increased permeability can be estimated. Approaches to measuring the instantaneous acoustic response level and cumulative acoustic response dose are provided, for example, in International Application No. PCT/US18/33815, filed on May 22, 2018, the entire disclosure of which is incorporated herein by reference. In addition, approaches to configuring the transducer array for detecting the acoustic signals from the microbubbles are provided, for example, in U.S. Patent Application No. 62/681,282, filed on Jun. 6, 2018, the contents of which are incorporated herein by reference.

Figure 5:
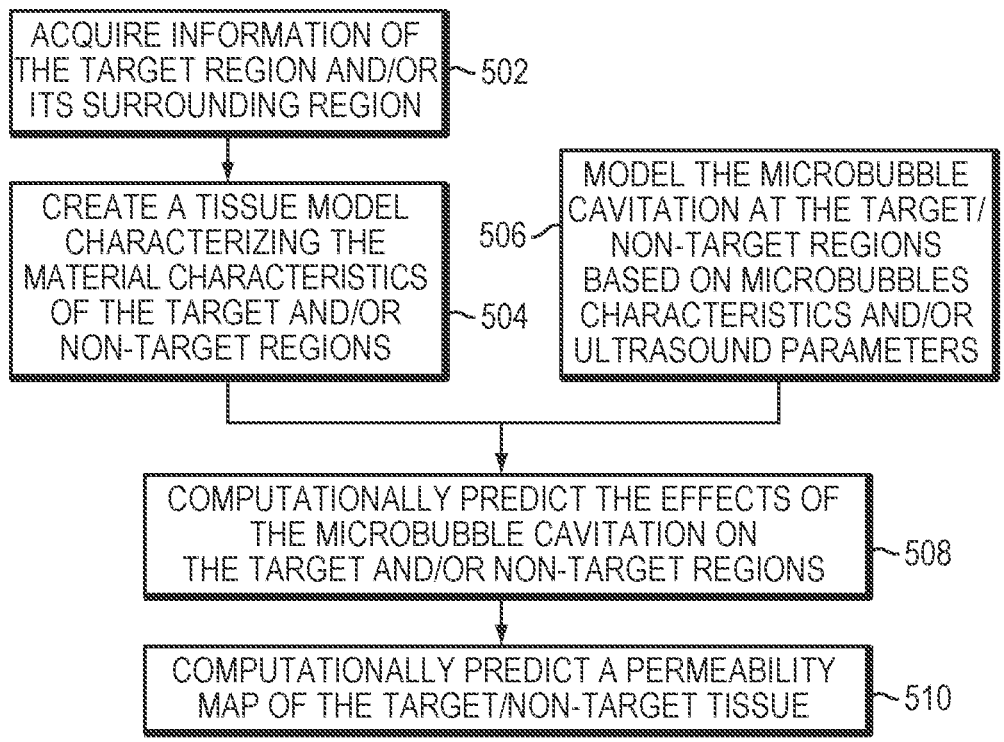
FIG. 5 is a flow chart illustrating an approach of computationally generating a permeability map in accordance with various embodiments.

Additionally or alternatively, the permeability map 402 may be created at the planning stage. Generally, the degree of tissue permeability and/or the volume of tissue with increased permeability correlates predictably with the microbubble characteristics (e.g., the concentration) and/or the ultrasound parameters, such as the delivered acoustic power (or power density) and energy in the target region 202. Thus, by synchronizing the distribution of the acoustic power emission with microbubble administration, the degree of tissue permeability can be reliably estimated by computing the cumulative expected cavitation or other acoustic effect during the sonication procedure and/or actually simulating the sonication computationally. For example, referring to FIG. 5, in various embodiments, prior to implementing a computational simulation for predicting the permeability map, information of the target tissue and/or non-target tissue is first acquired (in step 502). In one embodiment, the tissue information is determined, manually or automatically using conventional tissue-analysis software, based on images acquired by the imager 122. In a second step 504, the computational simulation creates a tissue model characterizing the material characteristics of the target and/or non-target regions based on the information thereof. The tissue model may take the form of a 3D table of cells corresponding to the voxels representing the target and/or non-target tissue; the values of the cells represent characteristics of the tissue, such as heat tolerance, that are relevant to disruption of the tissue. The voxels are obtained tomographically by the imager 122 and the type of tissue that each voxel represents can be determined automatically, once again, by conventional tissue-analysis software. Using the determined tissue types and a lookup table of tissue parameters (e.g., heat tolerance by type of tissue), the cells of the tissue model may be populated. Further detail regarding creation of a tissue model that identifies the heat sensitivity and/or thermal energy tolerance of various tissues may be found in U.S. Patent Publication No. 2012/0029396, the entire disclosure of which is hereby incorporated by reference.

In addition, the simulation may computationally model the microbubble cavitation at the target/non-target regions based on the characteristics (e.g., administration profile, size distribution, concentration, etc.) of the microbubbles to be introduced and/or the applied ultrasound parameters (e.g., amplitude, frequency, duration of the sonication pulses, etc.) (in a step 506). In some embodiments, based on the modeled microbubble cavitation and the established tissue model, the simulation computationally predicts the effects of the microbubble cavitation on the target and/or non-target regions (in a step 508). Subsequently, a permeability map 402 of the target/non-target tissue resulting from the microbubble-enhanced ultrasound procedure is computationally predicted (in a step 510). Approaches to computationally simulating effects of microbubble cavitation on the target/non-target regions, and based thereon generating the permeability map 402 are provided, for example, in U.S. Patent Application entitled "Simulation-Based Drug Treatment Planning" filed on even date herewith, the contents of which are incorporated herein by reference.

The permeability map generated using the MRI contrast agent, the localized acoustic response or the computational simulation, alone or in combination with one another, may be compared against the 3D voxel set of the target volume 202 acquired prior to the ultrasonic procedure. Again, based on the comparison, the tissue permeability in the target region 202 may be verified to ensure that the therapeutic drug can be effectively penetrate and/or diffuse therein.

In various embodiments, after application of the first series of sonications and generation of the permeability map 402, the therapeutic agent is administered into the target volume 202 based on the permeability map 402. Because the therapeutic agent may itself exhibit responsiveness to sonication and/or enhance the disruption rate of the target tissue, this approach may advantageously increase the uptake rate (including, for example, the penetration rate, release rate and/or activation rate) of the therapeutic agent in the target region. In addition, in this situation, it may not be necessary to obtain and verify a new permeability map for a subsequent sonication and/or drug administration.

Figure 6:
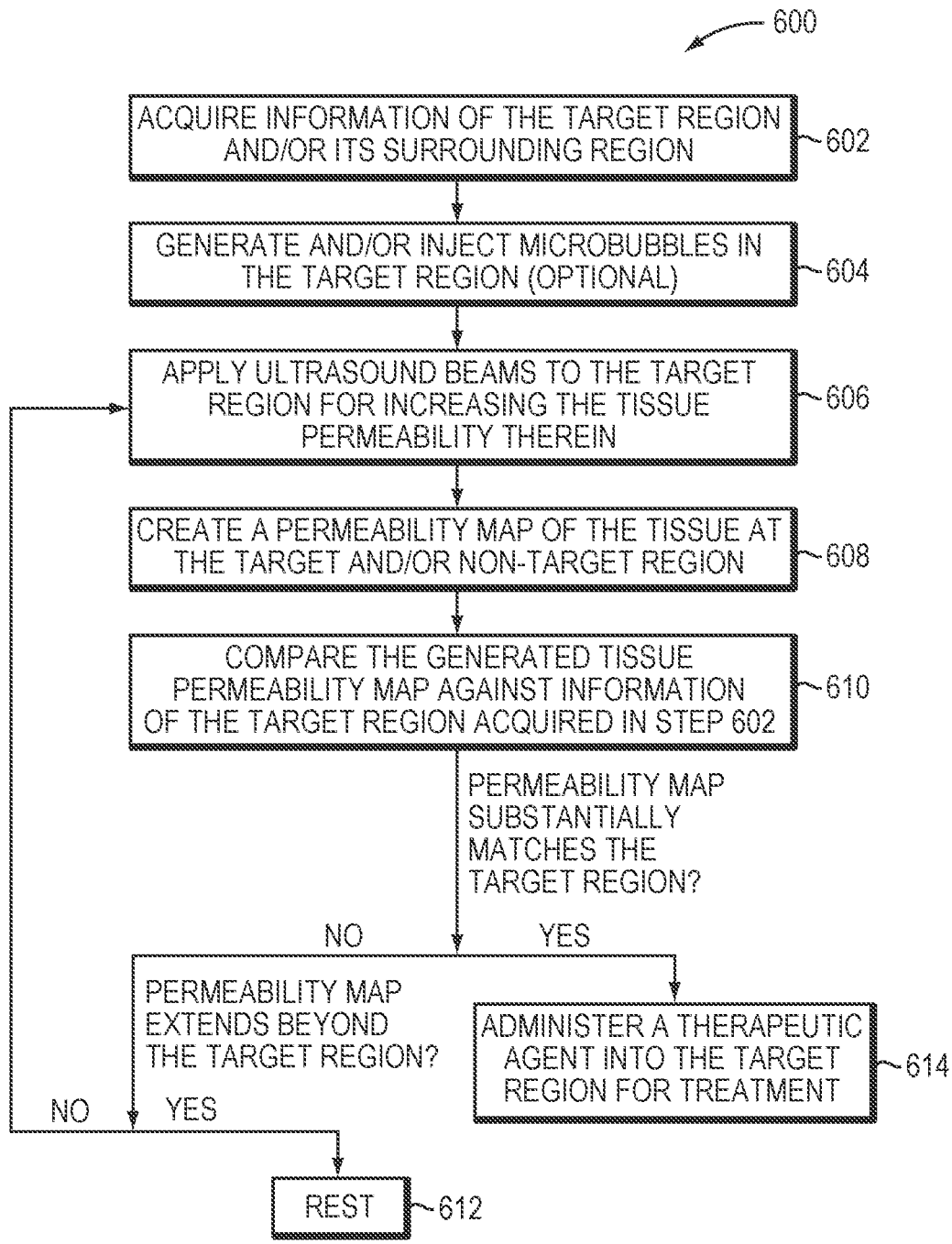
FIG. 6 is a flow chart illustrating an approach of applying ultrasound sonication to enhance targeted drug delivery by temporarily increasing tissue permeability in the target region in a controlled and reversible manner in accordance with various embodiments of the present invention.

FIG. 6 illustrates a representative approach 600 using ultrasound sonication to enhance targeted drug delivery by temporarily increasing tissue permeability in the target region in a controlled and reversible manner. In a first step 602, an imager (e.g., an MRI device) 122 is utilized to acquire information (such as the location, size, or shape) of the target region and/or non-target region prior to applying the ultrasound sonication; the target information may include a 3D set of voxels corresponding to the target region, and in some cases, the voxels include attributes specifying tissue characteristics. Optionally, in a second step 604, microbubbles may be injected and/or generated in the target region for promoting disruption of the tissue, thereby increasing tissue permeability. For example, the microbubbles may be generated by applying ultrasound pulses having an energy above a threshold. Additionally or alternatively, the microbubbles may be injected using the administration system 126. In a third step 606, based on the defined target information, converging ultrasound beams are applied to the target region so as to disrupt the tissue and increase tissue permeability therein. The tissue disruption (and consequent increase in tissue permeability) may also result from microbubble cavitation if the microbubbles are present in the target region. In a fourth step 608, a permeability map of the tissue at the target and/or non-target region is generated utilizing approaches described above (e.g., using the MRI contrast agent, the localized acoustic response and/or the computational simulation). In a fifth step 610, the tissue permeability map is compared against the target volume acquired in step 602 to verify a substantial match therebetween. Steps 606-610 may be iteratively performed until the tissue region having adequately increased permeability substantially matches the defined target volume. In some embodiments, when the disrupted tissue region on the permeability map is larger than the target volume identified in step 602, the patient is required to rest for one or two days until the tissue at the target/non-target region has regenerated and lost the induced permeability (and so can be disrupted again from the baseline level) (in a step 612). Finally, in a step 614, the therapeutic agent is administered into the target region for treatment.

In general, functionality for increasing tissue permeability in a target region, including, for example, analyzing imaging data of the target and/or non-target regions acquired using an imager 122, determining a 3D voxel set of a target volume based on the imaging data, creating a tissue model characterizing the material characteristics of the target/non-target regions based on the imaging data, modeling microbubble cavitation at the target/non-target regions based on microbubbles characteristics and/or ultrasound parameters, computationally predicting the effects of the microbubble cavitation on the target/non-target regions, computationally predicting a permeability map of the target/non-target tissue, causing microbubbles to be generated and/or injected in the target region, causing ultrasound beams to be applied to the target region for increasing the tissue permeability therein, causing the MRI contrast agent to be introduced to the target/non-target region and generating a permeability map based thereon, comparing the generated tissue permeability map against the 3D voxel set of a target volume identified in the images, and/or causing a therapeutic agent to be administered into the target region for treatment, as described above, whether integrated within a controller of the imager 122, and/or an ultrasound system 100, or provided by a separate external controller or other computational entity or entities, may be structured in one or more modules implemented in hardware, software, or a combination of both. The ultrasound controller 108 and/or MR controller 148 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The therapeutic agent may include any drug that is suitable for treating a tumor. For example, for treating glioblastoma (GBM), the drug may include or consist of, e.g., one or more of Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, Cytarabine (cytosine arabinoside, ara-C)/ara-U, etc.

In addition, for treating GBM, those skilled in the art can select a drug and a BBB opening regime optimized to enhance drug absorption across the BBB within patient safety constraints. In this regard, it is known that the BBB is actually already disrupted in the core of many tumors, allowing partial penetration of antitumor drugs; but the BBB is widely intact around the "brain adjacent to tumor" (BAT) region where invasive/escaping GBM cells can be found, and which cause tumor recurrence. Overcoming the BBB for better drug delivery within the tumor core and the BAT can be accomplished using ultrasound as described herein. The drugs employed have various degrees of toxicity and various penetration percentages through the BBB. An ideal drug has high cytotoxicity to the tumor and no BBB penetration (so that its absorption and cytotoxic effects can be confined to regions where the BBB is disrupted), low neurotoxicity (to avoid damage to the nervous system), and tolerable systemic toxicity (e.g., below a threshold) at the prescribed doses. The drug may be administered intravenously or, in some cases, by injection proximate to the tumor region. In addition, configurations of the administration system 126 for introducing microbubbles and/or therapeutic agent into the target region 202 may be found in U.S. patent application Ser. No. 62/597,076, the contents of which are incorporated herein by reference.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for causing a disruption of a target tissue for treatment and evaluating the disruption of the target tissue, the system comprising a controller configured to:
   prior to causing the disruption of the target tissue, cause an imaging device to acquire a digital representation of at least a portion of a target volume of the target tissue;
   cause the disruption of the target tissue in a region corresponding to the target volume by causing an ultrasound transducer to generate and deliver at least one sonication of shaped energy beams to the target volume so as to increase tissue permeability therein;
   subsequent to causing the disruption of the target tissue, generate a tissue permeability map indicating regions of increased tissue permeability and estimates of the tissue permeability due to the disruption of the target tissue and computationally evaluate, based on the tissue permeability map, the disruption of the target tissue within the target volume;
   compare (i) a mapped region of the tissue permeability map having increased permeability due to the disruption of the target tissue to (ii) the digital representation of the target volume acquired using the imaging device prior to causing the disruption of the target tissue; and
   determine that a therapeutic agent should be administered into the target volume only when, based on the comparing, there is a substantial match between (i) the mapped region of the tissue permeability map having increased permeability due to the disruption at the target tissue and (ii) the digital representation of the target volume acquired using the imaging device prior to causing the disruption of the target tissue.

2. The system of claim 1, wherein the controller is further configured to computationally determine, based on the tissue permeability map, whether tissue within the target volume can admit the therapeutic agent.

3. The system of claim 2, wherein the controller is further configured to determine that the therapeutic agent should only be administered when tissue within the target volume can admit the therapeutic agent.

4. The system of claim 2, wherein the controller is further configured to computationally determine whether tissue within the target volume can admit the therapeutic agent based on a molecular size thereof and the estimates of the tissue permeability.

5. The system of claim 2, wherein the controller is further configured to computationally verify, based on the tissue permeability map, that tissue outside the target volume cannot admit the therapeutic agent to a degree that would trigger an onset of damage.

6. The system of claim 2, wherein the therapeutic agent comprises at least one of Busulfan, Thiotepa, CCNU (lomustine), BCNU (carmustine), ACNU (nimustine), Temozolomide, Methotrexate, Topotecan, Cisplatin, Etoposide, Irinotecan /SN-38, Carboplatin, Doxorubicin, Vinblastine, Vincristine, Procarbazine, Paclitaxel, Fotemustine, Ifosfamide /4-Hydroxyifosfamide /aldoifosfamide, Bevacizumab, 5-Fluorouracil, Bleomycin, Hydroxyurea, Docetaxel, or Cytarabine (cytosine arabinoside, ara-C)/ara-U.

7. The system of claim 1, wherein the controller is further configured to cause the ultrasound transducer to generate and deliver at least a second sonication of shaped energy beams to the target volume after administering the therapeutic agent.

8. The system of claim 1, wherein the tissue permeability map includes a plurality of permeability levels, each permeability level associated with a tissue region in the target volume and indicating a maximal size of molecules capable of entering the associated tissue region.

9. The system of claim 8, wherein the controller is further configured to determine that the therapeutic agent should be administered into the target volume based on the permeability levels.

10. The system of claim 1, wherein the controller is further configured to generate the tissue permeability map based at least in part on at least one of MRI contrast imaging, planning or simulation of the at least one sonication, or an acoustic response of the target volume during the disruption.

11. The system of claim 1, wherein the controller is further configured to cause the imaging device to acquire an image of the target volume during delivery of the at least one sonication and the controller is further configured to adjust a parameter associated with a subsequent sonication based on the image.

12. The system of claim 1, wherein the controller is further configured to cause the ultrasound transducer to generate a plurality of sonications each delivering shaped acoustic energy to one of a plurality of focal zones in the target volume, the focal zones collectively being coextensive with the target volume.

13. The system of claim 1, wherein the at least one sonication causes generation and cavitation of microbubbles in the target volume.

14. The system of claim 13, wherein the controller is further configured to determine that a microbubble seed should be administered to the target volume, wherein the at least one sonication and the microbubble seed cause generation of the microbubbles.

15. The system of claim 1, wherein the controller is further configured to determine that microbubbles should be administered to the target volume, wherein the at least one sonication causes cavitation of the microbubbles.

16. The system of claim 1, wherein the mapped region of the tissue permeability map having increased permeability substantially matches the digital representation of the target volume if the mapped region of the tissue permeability map having increased permeability and the digital representation of the target volume are substantially coextensive spatially.

17. The system of claim 1, wherein the controller is further configured to, prior to determining that the therapeutic agent should be administered into the target volume, cause a subsequent disruption of the target tissue in the region corresponding to the target volume so as to further increase tissue permeability therein if the mapped region of the tissue permeability map having increased permeability is smaller than the digital representation of the target volume.

18. The system of claim 1, wherein the controller is further configured to, prior to determining that the therapeutic agent should be administered into the target volume, require a rest period to reduce tissue permeability therein if the mapped region of the tissue permeability map having increased permeability is larger than the digital representation of the target volume.

* * * * *